United States Patent
Rayhanabad

(10) Patent No.: US 11,389,622 B1
(45) Date of Patent: Jul. 19, 2022

(54) PATCH FOR PROVIDING DIALYSIS

(71) Applicant: Simon B. Rayhanabad, Huntington Beach, CA (US)

(72) Inventor: Simon B. Rayhanabad, Huntington Beach, CA (US)

( * ) Notice: Subject to any disclaimer, the term of this patent is extended or adjusted under 35 U.S.C. 154(b) by 0 days.

(21) Appl. No.: 17/329,118

(22) Filed: May 24, 2021

Related U.S. Application Data

(63) Continuation-in-part of application No. 17/163,375, filed on Jan. 30, 2021, which is a continuation of application No. 16/186,555, filed on Nov. 11, 2018, now Pat. No. 10,905,856.

(60) Provisional application No. 62/673,766, filed on May 18, 2018, provisional application No. 62/634,663, filed on Feb. 23, 2018, provisional application No. 62/599,441, filed on Dec. 15, 2017, provisional application No. 62/585,490, filed on Nov. 13, 2017.

(51) Int. Cl.
| | |
|---|---|
| *A61M 25/02* | (2006.01) |
| *A61M 1/14* | (2006.01) |
| *A61M 1/36* | (2006.01) |
| *A61M 39/02* | (2006.01) |

(52) U.S. Cl.
CPC .............. *A61M 25/02* (2013.01); *A61M 1/14* (2013.01); *A61M 1/3655* (2013.01); *A61M 39/0208* (2013.01); *A61M 39/0247* (2013.01); *A61M 2025/0266* (2013.01); *A61M 2025/0286* (2013.01)

(58) Field of Classification Search
CPC ...... A61M 1/14; A61M 1/3655; A61M 25/02; A61M 2025/0266; A61M 2025/0286; A61M 39/0208; A61M 39/0247
See application file for complete search history.

(56) References Cited

U.S. PATENT DOCUMENTS

| | | | | |
|---|---|---|---|---|
| 6,206,913 | B1 * | 3/2001 | Yencho | A61B 17/11 606/153 |
| 7,828,781 | B2 * | 11/2010 | Edoga | A61M 1/3655 604/288.02 |
| 2003/0100920 | A1 * | 5/2003 | Akin | A61F 2/064 606/213 |
| 2004/0102796 | A1 * | 5/2004 | Hill | A61B 17/11 606/153 |
| 2005/0171565 | A1 * | 8/2005 | Yencho | A61B 17/11 606/153 |
| 2008/0176271 | A1 * | 7/2008 | Silver | A61B 5/6882 435/29 |
| 2008/0255609 | A1 * | 10/2008 | Opie | A61B 17/0057 606/213 |
| 2009/0035346 | A1 * | 2/2009 | Nugent | C12N 5/069 435/405 |
| 2010/0204783 | A1 * | 8/2010 | Nugent | A61M 1/3655 623/1.41 |
| 2011/0213309 | A1 * | 9/2011 | Young | A61M 1/3661 604/175 |

(Continued)

*Primary Examiner* — Benjamin J Klein
(74) *Attorney, Agent, or Firm* — Steven R. Vosen

(57) ABSTRACT

An apparatus for providing dialysis is described. The apparatus is a patch which provides structural support to a blood vessel, such as vein or fistula. The patch provides a location for puncturing the blood vessel with a needle, either at the puncture site or on the back side to prevent the needle from going through the blood vessel. The patch may also be palpated, allowing health care provider to easily locate a preferred puncture site.

21 Claims, 6 Drawing Sheets

(56) References Cited

U.S. PATENT DOCUMENTS

2012/0245536 A1* 9/2012 Gerber .............. A61M 39/0208
                                                      604/288.02
2018/0289939 A1* 10/2018 Mason .............. A61M 39/0247

* cited by examiner

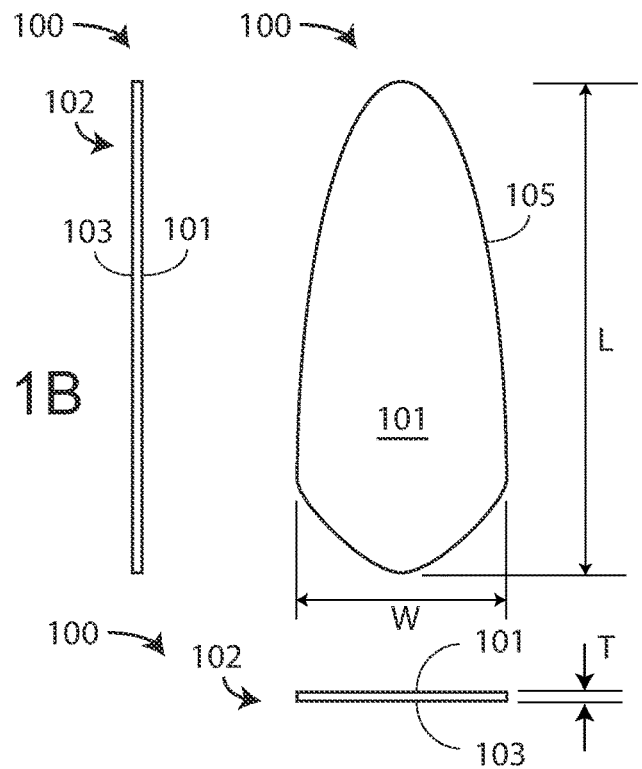
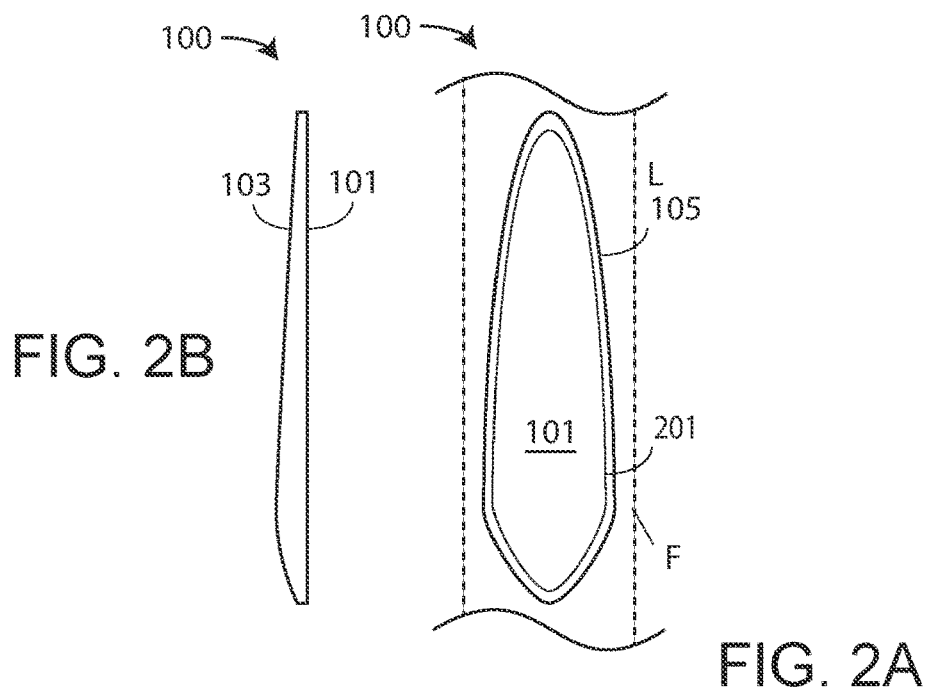
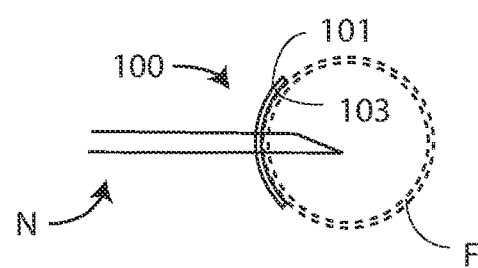
FIG. 1A  FIG. 1B  FIG. 1C
FIG. 2A  FIG. 2B  FIG. 2C

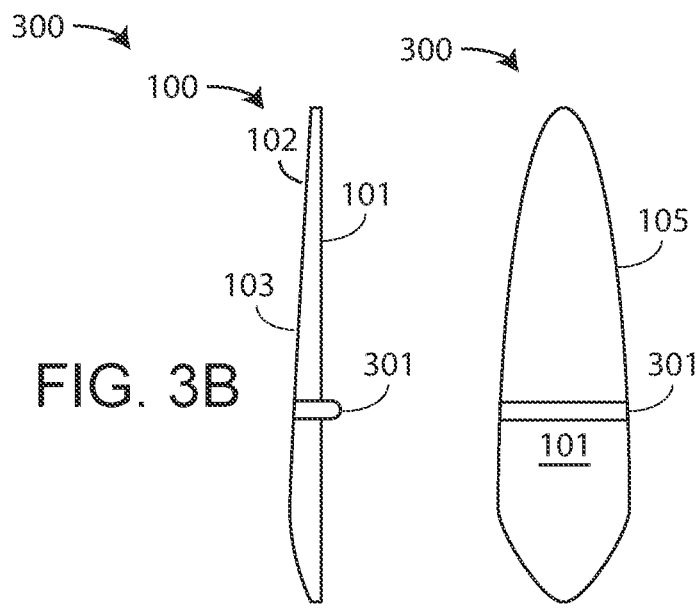
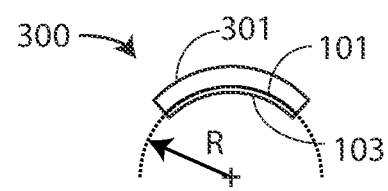
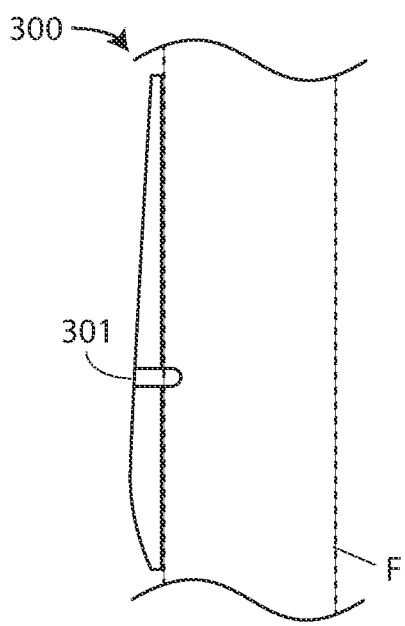
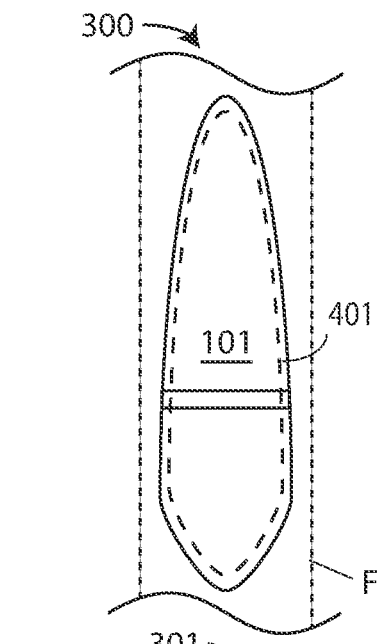
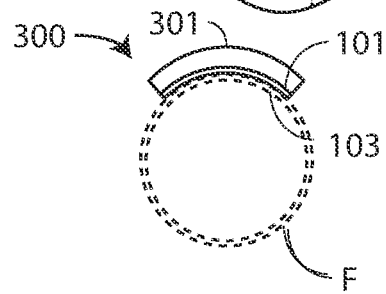

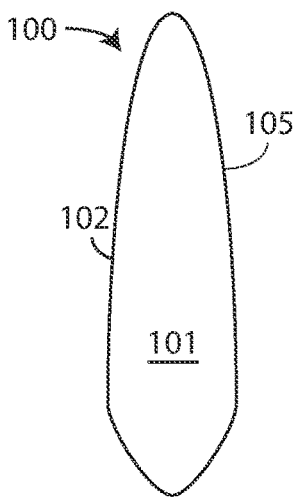
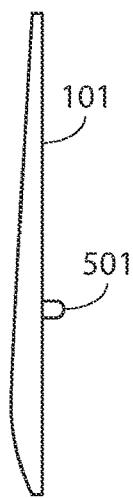
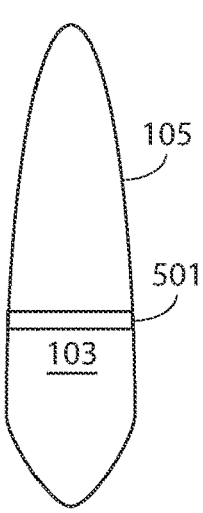
FIG. 5A    FIG. 5B    FIG. 5D
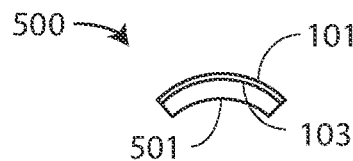
FIG. 5C
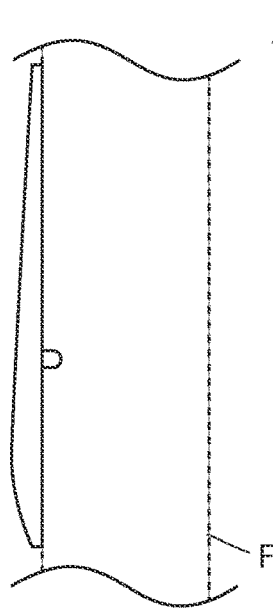
FIG. 6B
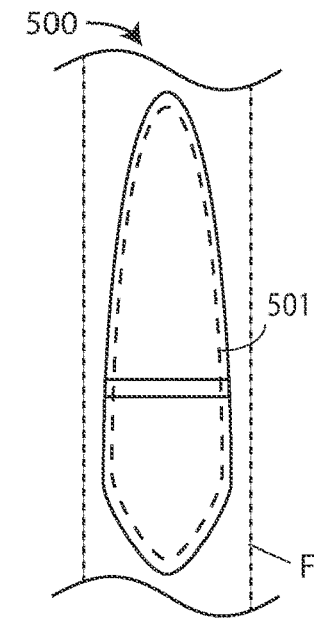
FIG. 6A
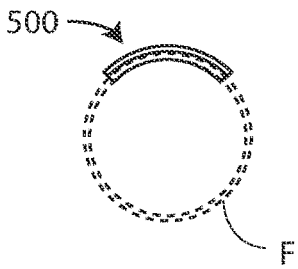
FIG. 6C

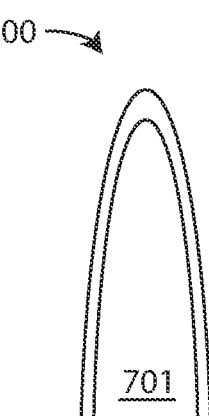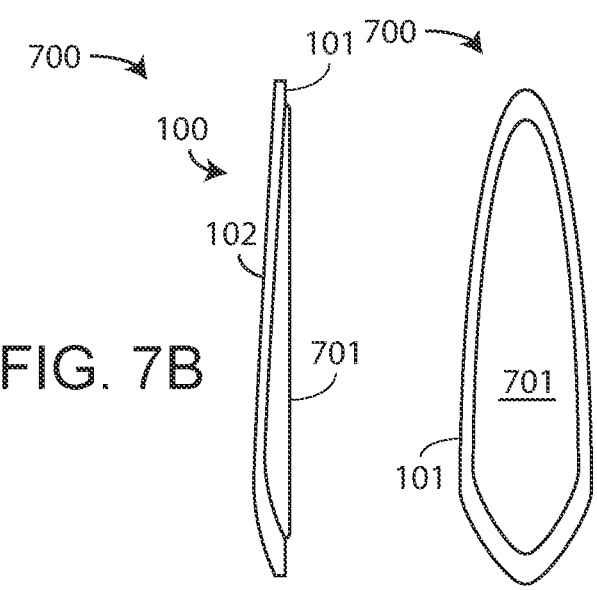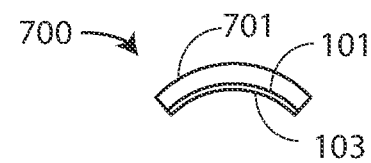
FIG. 7B  FIG. 7A
FIG. 7C
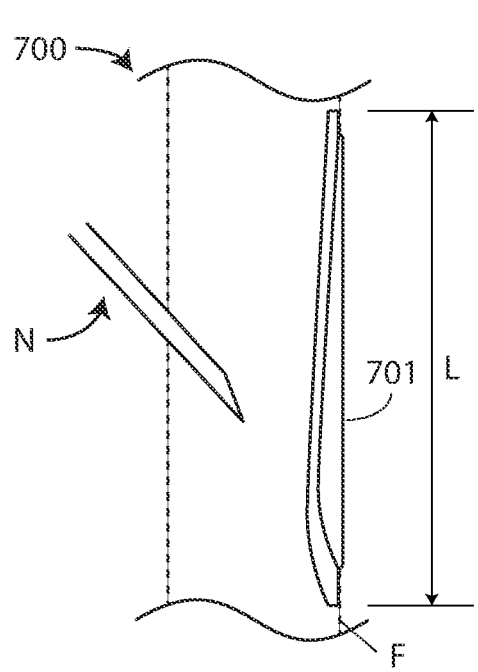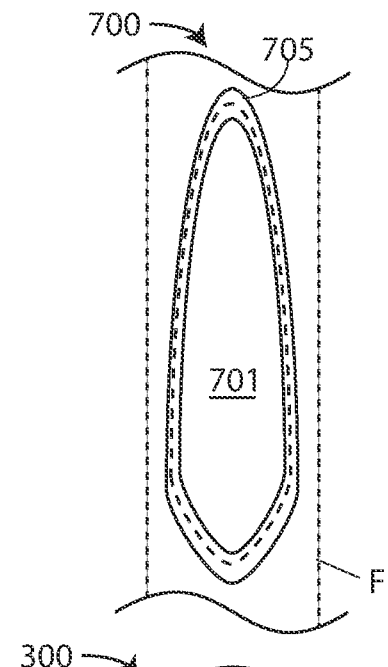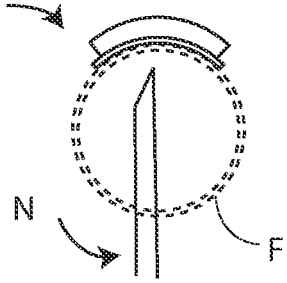
FIG. 8A
FIG. 8B  FIG. 8C

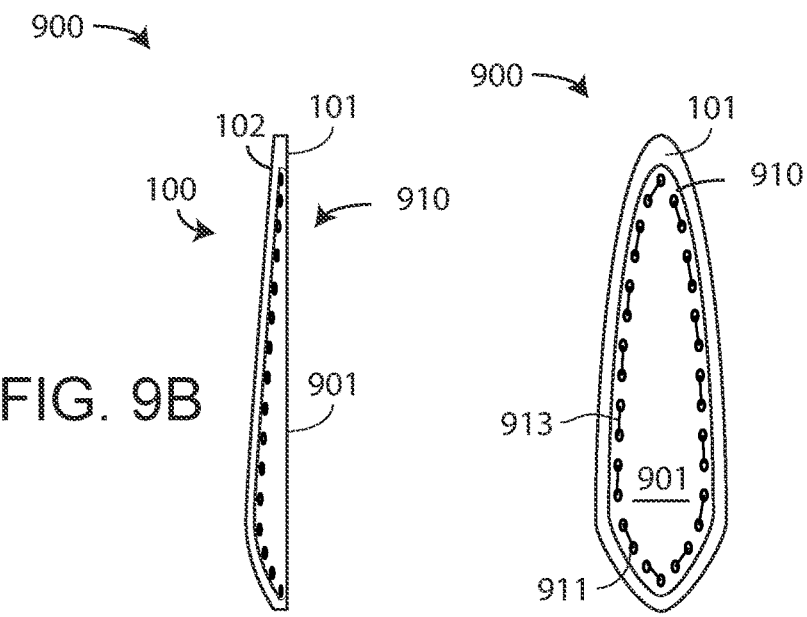
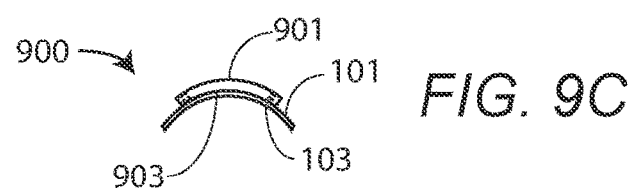
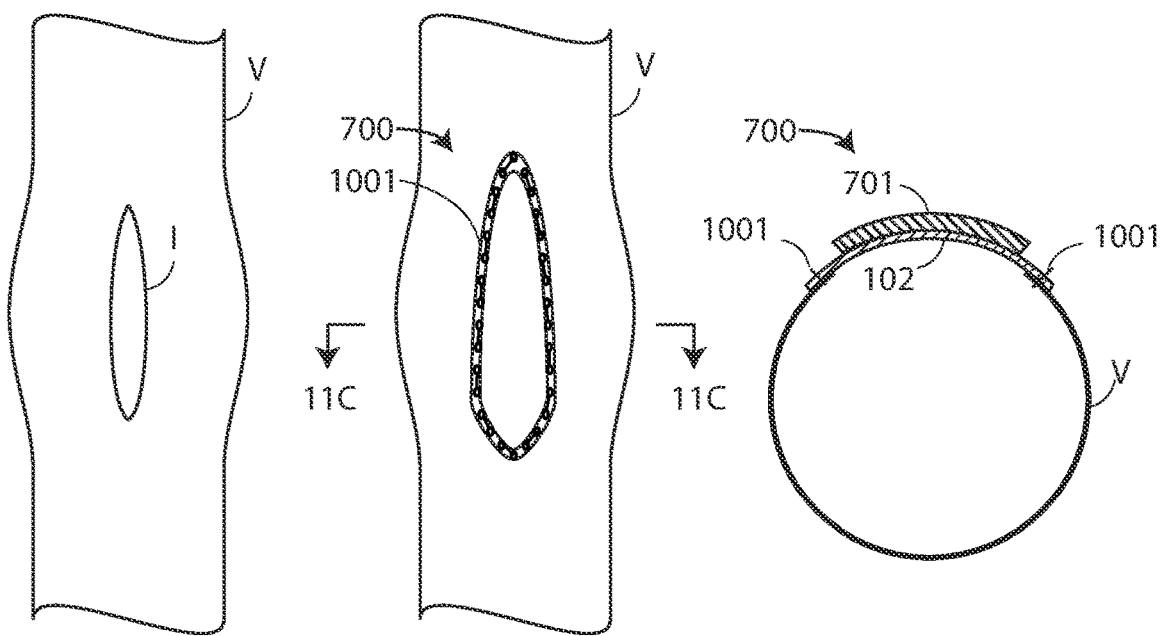

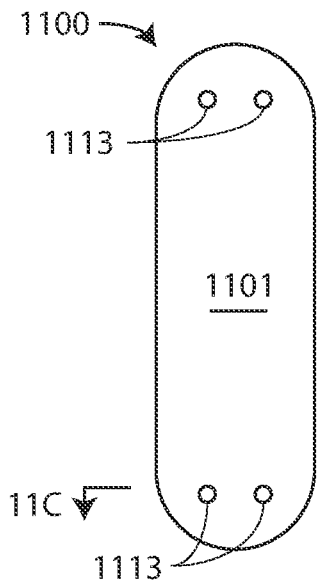
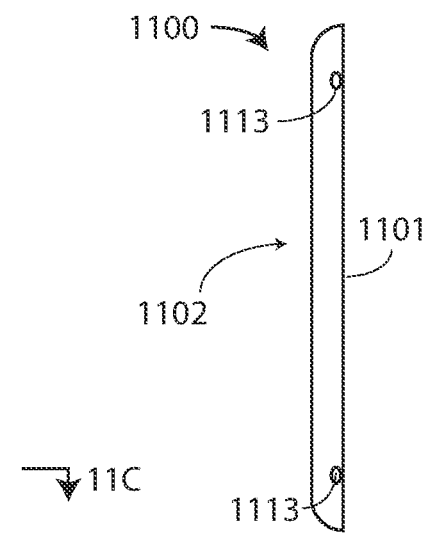
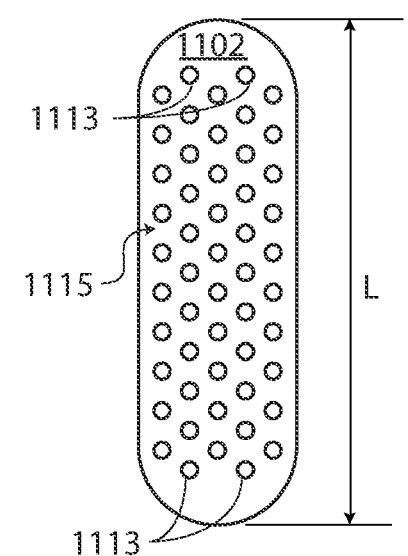
FIG. 11A       FIG. 11B       FIG. 11C
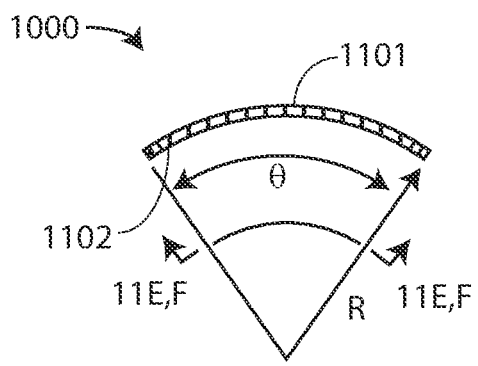
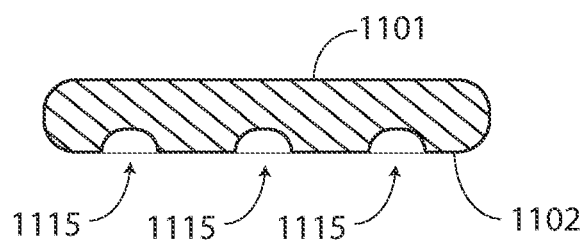
FIG. 11D       FIG. 11E
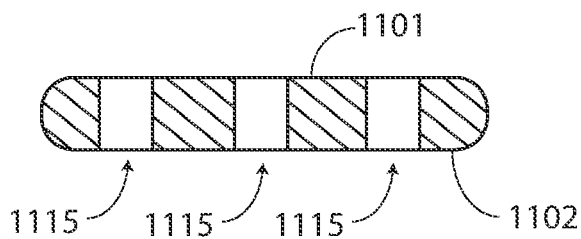
FIG. 11F

PATCH FOR PROVIDING DIALYSIS

CROSS-REFERENCE TO RELATED APPLICATIONS

This application is a continuation-in-part of application Ser. No. 17/163,375, filed Jan. 30, 2021, which is a continuation of application Ser. No. 16/186,555, filed Nov. 11, 2018, which claims the benefit of U.S. Provisional Applications No. 62/585,490, filed Nov. 13, 2017, U.S. Provisional Applications No. 62/599,441, filed Dec. 15, 2017, U.S. Provisional Applications No. 62/634,663, filed Feb. 23, 2018, and U.S. Provisional Applications No. 62/673,766, filed May 18, 2018, the contents of which are hereby incorporated by reference in their entirety.

BACKGROUND OF THE INVENTION

Field of the Invention

The present invention generally relates to dialysis, and more particularly to a method and system for surgically preparing a patient for dialysis.

Discussion of the Background

Background

In hemodialysis, an artificial kidney is used to remove waste and extra chemicals and fluid from a patient's blood. Typically, blood is removed from a first location in the patient's circulation system, is filtered, and is provided back into the patient at a second location that is downstream from the first location.

Vascular access is obtained from a minor surgical procedure to the arm or leg. In some cases, an access is obtained by joining an artery to a vein to form a bigger blood vessel to form a fistula.

The nature of hemodialysis requires vascular access that is suitable for repeated puncture and allows a high blood flow rate for high-efficiency hemodialysis with minimal complications. Over time, however, complications may arise, due in part to the weakening of the blood vessels due to repeated puncturing.

There is a need in the art for a device, and method of using such a device, that extends the life of vascular access for hemodialysis.

BRIEF SUMMARY OF THE INVENTION

The present invention overcomes the disadvantages of prior art by providing a patch for a blood vessel.

Certain embodiments provide a patch for a blood vessel comprising: a rigid portion having an inner surface with a length extending along a longitudinal direction of a cylindrical shape and a width that extends circumferentially along only a portion of the circumference of the cylindrical shape, and an outer surface opposing the inner surface, such that the patch is adapted to cover a portion of the blood vessel.

Certain other embodiments provide a patch for a blood vessel comprising: a rigid portion having an inner surface with a length extending along a longitudinal direction of a cylindrical shape and a width that extends circumferentially along only a portion of the circumference of the cylindrical shape, and an outer surface opposing the inner surface, where the rigid portion includes stainless steel or titanium, and where said inner surface includes three-dimensional features having a dimension of from 0.25 mm to 2 mm, such that the patch is adapted to cover a portion of the blood vessel and inhibit needles from moving along the inner surface.

These features together with the various ancillary provisions and features which will become apparent to those skilled in the art from the following detailed description, are attained by the patch of the present invention, preferred embodiments thereof being shown with reference to the accompanying drawings, by way of example only, wherein:

BRIEF DESCRIPTION OF THE SEVERAL VIEWS OF THE DRAWING

FIGS. 1A, 1B, and 1C are a top view, a side view, and a front view, respectively, of a first embodiment patch;

FIGS. 2A, 2B, and 2C are a top view, a side view, and a front view, respectively, of the patch of FIG. 1A as attached to a fistula;

FIGS. 3A, 3B, and 3C are a top view, a side view, and a front view, respectively, of a second embodiment patch;

FIGS. 4A, 4B, and 4C are a top view, a side view, and a front view, respectively, of the patch of FIG. 3A as attached to a fistula;

FIGS. 5A, 5B, 5C, and 5D are a top view, a side view, a front view, and back view, respectively, of a third embodiment patch;

FIGS. 6A, 6B, and 6C are a top view, a side view, and a front view, respectively, of the patch of FIG. 5A as attached to a fistula;

FIGS. 7A, 7B, and 7C are a top view, a side view, and a front view, respectively, of a fourth embodiment patch;

FIGS. 8A, 8B, and 8C are a top view, a side view, and a front view, respectively, of the patch of FIG. 7A as attached to a fistula;

FIGS. 9A, 9B, and 9C are a top view, a side view, and a back view of a fifth embodiment patch;

FIGS. 10A, 10B, and 10C illustrate one use of the patch of FIG. 7A, where FIG. 10A shows an incision to a vein, FIG. 10B shows the patch sewn into the vein, and FIG. 10C is sectional view 10C-10C of FIG. 10B;

FIGS. 11A, 11B, 11C, 11D, and 11E are a top, a side, a bottom, an end view, and a sectional view 11E-11E of a sixth embodiment patch; and FIG. 11F is a sectional view 11F-11F of an alternative sixth embodiment patch.

Reference symbols are used in the Figures to indicate certain components, aspects or features shown therein, with reference symbols common to more than one Figure indicating like components, aspects or features shown therein.

DETAILED DESCRIPTION OF THE INVENTION

Embodiments are presented for a patch which is an aid to providing hemodialysis to a patient. The Specification and Figures illustrate various patches, which are affixed to fistula and which are then then surgically placed below the skin of a patient. Hemodialysis is thus provided by inserting the hemodialysis needle through the skin and then patch, and into the vein or fistula. The term "blood vessel" is used here to denote any blood-carrying vessel, including both natural and surgically provided vessels, such as a surgically provided fistula.

FIGS. 1A, 1B, and 1C are a top, side, and front view, respectively, of a first embodiment patch 100. Patch 100 includes a thickness of material 102 having an outer edge 105, a side 103 for placing against a patient's fistula, and a side 101 opposing side 103.

In one embodiment, material 102 is a biocompatible material, such as polytetrafluoroethylene (PTFE), formed into a fabric, such as Gore-Tex (W. L. Gore and Associates, Newark, Del.). The thickness of material 102 may be, for example and without limitation, approximately 0.50 mm, or may be 0.25 mm, 0.50 mm, 0.75 mm, or 1 mm.

In one embodiment, side 103 includes an optional coating 103 is provided as a barrier between the patient's fistula and material 102. Coating 103 may, for example and without limitation, have bactericidal properties, such as a coating of silver.

In another embodiment, material 102 is soft enough to enable a surgeon to sew the material, such as outer edge 105, to a blood vessel.

FIGS. 3A, 3B, and 3C are a top, side, and front view, respectively, of a second embodiment patch 300, which is generally similar to patch 100 in construction and use, except as explicitly noted.

Patch 300 includes a portion that stiffens, or reinforces, the patch, which is illustrated as reinforcement 301. Reinforcement 301 is more rigid than material 102, due to the material used or the shape or thickness of the reinforcement, and is in general provides a curvature to the patch 300. Thus, for example, reinforcement 301 may have a semicircular shape to match that of fistula F, as shown by radius R in FIG. 3C. The radius R may be, in various embodiments, from 2.5 mm to 3.5 mm, and the width W may be long enough to cover from 70 degrees to 180 degrees of the circumference of fistula F.

Reinforcement 301 may be formed integral with patch 300, or may be formed from the same or a different material that is affixed to the patch. FIGS. 3A, 3B, and 3C illustrate, for example and without limitation, a reinforcement 301 on side 101 having a length and circular cross-section, and which is bent to have a curvature that closely matches the curvature of the fistula to which it will be attached. In certain embodiment, reinforcement 301 is deformable and may be shaped by hand to change the curvature of patch 300. In one embodiment, reinforcement 301 is formed from a biocompatible material, such as polytetrafluoroethylene (PTFE), formed into a fabric, such as Gore-Tex (W. L. Gore and Associates, Newark, Del.), or a metal such as stainless steel or titanium.

FIGS. 5A, 5B, 5C, and 5D are a top, side, front and back view of a third embodiment patch 500, which is generally similar to patch 100 or 300 in construction and use, except as explicitly noted. In one embodiment, reinforcement element 501 is generally similar to reinforcement element 301, but is affixed to side 103.

FIGS. 7A, 7B, and 7C are a top, side, and front view of a fourth embodiment patch 700, which is generally similar to patch 100, 300 or 500 in construction and use, except as explicitly noted.

Patch 700 includes a reinforcement 701 which is attached to side 101. Reinforcement 701 covers substantially all of side 101, except for a border that protrudes from the edge of the reinforcement, and allows for stitching material 102 to the fistula. In one embodiment, reinforcement 701 is formed from a biocompatible material, such as polytetrafluoroethylene (PTFE), formed into a fabric, such as Gore-Tex (W. L. Gore and Associates, Newark, Del.), or a metal, such as a stainless steel or titanium. In yet another alternative embodiment, reinforcement 701 is a layered material, and may have a layer of a metal with a coating of a biocompatible material.

In another embodiment, the side of reinforcement 701 facing the interior of the fistula has three-dimensional surface features such as a roughened surface, or a surface covered with holes or protuberances on the order of the size of the tip needle N. The surface features of reinforcement 701 prevents the tip of needle from moving along the reinforcement element, and thus assist in making sure that the needle, when inserted into the patch, does not slip off of the edge of the patch and puncture an unprotected portion of the fistula.

FIGS. 9A, 9B, and 9C are a top, side, and front view of a fifth embodiment patch 900, which is generally similar to patch 100, 300, 500, or 700 in construction and use, except as explicitly noted.

Patch 900 includes material 102 and reinforcement 910. As shown in FIG. 9C, reinforcement 900 has an outer surface 901 and inner surface 903 and a plurality of holes 913 through the thickness of the reinforcement. Inner surface 903 that is affixed to side 101 of material 102 using thread 911, which passes through material 102 and holes 913. In alternative embodiments, material 102 and reinforcement 910 are affixed using an adhesive or other appropriate means of joining, As shown in FIG. 9A, reinforcement 901 covers substantially all of side 101, except for a border that protrudes from the edge of the reinforcement, and allows for stitching material 102 to the fistula, as shown above regarding patches 100, 300, 500, and 700.

In certain embodiments, patch 900 is applied to side of fistula F that is distal from the skin, and used as shown for patch 700. That is, patch 900 is rigid enough to prevent puncturing by a needle, and is placed on the back side of the fistula from where the catheter is connected to prevent a second puncture of the fistula. In certain other embodiments, material 102 of patch 900 is optional, and the patch comprises reinforcement 910, including outer surface 901, inner surface 903, and holes 913, and does not include material 102.

In one embodiment, reinforcement 901 is formed from a biocompatible material, such as polytetrafluoroethylene (PTFE), formed into a fabric, such as Gore-Tex (W. L. Gore and Associates, Newark, Del.), or a metal, such as a stainless steel or titanium. In another embodiment, the side of reinforcement 901 facing the interior of the fistula has three-dimensional surface features such as a roughened surface, or a surface covered with holes or protuberances on the order of the size of the tip needle N. The surface features of reinforcement 901 prevents the tip of needle from moving along the reinforcement element, and thus assist in making sure that the needle, when inserted into the patch, does not slip off of the edge of the patch and puncture an unprotected portion of the fistula.

FIGS. 11A, 11B, 11C, and 11D are a top, a side, a bottom, and an end view of a sixth embodiment patch 1100, and FIG. 11E is a sectional view 11E-11E of FIG. 11D. Patch 1100 is generally similar to patch 100, 300, 500, 700, or 900 except as explicitly noted.

Patch 1100 is formed from a metal, such as a stainless steel or titanium and has the shape of a portion of a cylinder and has an outer surface 1101 and an outer surface 1102. In certain embodiment, patch 1100 is form from a metal having a thickness of from between 0.5 mm to 1.0 mm with a length L between 3 cm to 7 cm. In certain embodiments, the width of patch 1100 is such that it covers an angle, $\theta$, about a diameter that is in the range of from 70 degrees to 180 degrees. In certain other embodiments, the angle, $\theta$, is from 70 degrees to 90 degrees, from 90 degrees to 120 degrees, from 120 degrees to 150 degrees, or from 150 degrees to 180 degrees. In other embodiments, θ is 70 degrees, 80 degrees, 90 degrees, 100 degrees, 110 degrees, 120 degrees, 130 degrees, 140 degrees, 150 degrees, 160 degrees, 170 degrees, or 180 degrees.

As shown in FIGS. 11A-11C, patch 1100 includes holes 1113 extending from inner surface 1101 to outer surface 1102. As described subsequently, holes 1113 may be used for sewing or otherwise affixing the patch to a vessel, such as a fistula.

As shown in FIGS. 11C and 11E, inner surface 1102 includes three-dimensional features 1115 which may be a roughened surface, or a surface covered with holes or protuberances. In certain embodiments, the holes have a diameter selected to prevent a needle from moving along the inner surface. Thus, for example and without limitation, features 1115 may have a diameter, without limitation, of from 0.25 mm to 2 mm, such as, for example 1.0 mm, or otherwise sized to engage with the tip of a needle, such as a 18 French gauge needle.

FIG. 11E is a sectional view 11E-11E of FIG. 11D illustrating an alternative sixth embodiment patch, where features 1115 are holes through the thickness of patch 1100.

In certain embodiments, features 1115 on the order of the size of the tip needle N. Features 1115 thus prevent the tip of needle from moving inner surface 1102, and thus assist in making sure that the needle, when inserted into the patch, does not slip off of the edge of the patch and puncture an unprotected portion of the fistula.

Features 1115 illustrated in the figure are illustrative of the number, distribution, and size of the features. Thus, for example, feature 1115 may be a combination of holes and protuberances, and may be distributed as a regular pattern or as a random pattern on patch 1100.

Examples of various uses of the inventive patch is now presented. While these uses are presented with specific patch embodiments, such as patch 100, 300, 500, 700, 900, or 1100, this discussion is meant to be general and is not meant to limit the use of the various embodiments. Further, the vessels to which the patch is attached is meant to be illustrative and is not meant to limit the scope of the invention. Thus, while patch 100 is shown below attached to a fistula, and being used for providing hemodialysis, it will be understood by those skilled in the art that patch 100, or any of the other patches described herein, are useful in providing structural support to body parts, such as, in general, blood vessels, and may be so used. Thus, for example and without limitation, the inventive patch may be placed on a vein to provide structural support to the vein.

FIGS. 2A, 2B, and 2C are a top, side, and front view, respectively, of patch 100 as being attached to a fistula F by placing one side of patch 100, such as side 103, against fistula F and suturing material 102 near edge 105, as illustrated by dashed line 201.

As is best illustrated in FIG. 2C, patch 100 has the shape of a portion of a cylinder, of radius R, and thus extends partially around the outside of the circumference of the fistula, over a length L of the fistula, and on the side of fistula F that is proximal to the skin. FIG. 2C illustrates a needle N, which was previously inserted through the skin of the patient (not shown), and into fistula F somewhere along the fistula length L through patch 100. The length, L, is, in various embodiments, from 3 cm to 7 cm.

The use of patch 100, as in FIG. 2C, allows for repeated puncturing of the blood vessel without damaging the wall of the blood vessel. Patch 100 may also be located by palpation, allowing easier access to the blood vessel.

FIGS. 4A, 4B, and 4C are a top, side, and front view, respectively, of patch 300 as attached to fistula F by placing side 103 against fistula F and suturing material 102 near edge 105, as illustrated by dashed line 401. FIG. 4C illustrates how the curvature of patch 300 matches or approximates the curvature of fistula F. In one embodiment, patch 300 is provided on the side of fistula F that is proximal to the skin, and is used in a matter similar to that shown in FIG. 2C.

FIGS. 6A, 6B, and 6C are a top, side, and front view, respectively, of patch 500 as attached to fistula F by placing one side of patch 500, such as side 103 against fistula F and suturing material 102 near edge 105, as illustrated by dashed line 501.

In one embodiment, a patient is prepared for hemodialysis by forming a fistula from an artery and a vein of the patient, as is known in the art, and then by covering at least a portion of the outer surface of the fistula with a patch, which may be similar to 100, 300, 500, 700, 900, or 1100. The fistula and patch is then surgically placed below the skin of a patient. In preparing for hemodialysis, the catheter of the hemodialysis machine is place through the skin (not shown), through the patch, and into the fistula.

FIGS. 8A, 8B, and 8C are a top, side, and front view, respectively, of the patch 700 as attached, illustratively, to fistula F. As noted above, the purpose of patch 700 is to prevent puncture of the back side of fistula F by needle N.

In one embodiment, patch 700 is applied to fistula F by placing one side of patch 700, such as side 103 against fistula F and suturing material 102 near edge 105, as illustrated by dashed line 705. Patch 700 is placed on the side of the fistula that is distal from the skin, and thus from where a needle N is inserted, as shown in FIGS. 8B and 8C. Specifically, the needle N is inserted through the fistula somewhere along the fistula length L which is covered by patch 700. Reinforcement 701 is thus sufficiently strong, rigid, dense, or thick to prevent a needle tip from puncturing the material when the reinforcement is provided to fistula F.

FIGS. 11A, 11B, and 11C illustrate one use of the patch 700, where FIG. 11A shows an incision to a vein, FIG. 11B shows the patch sewn into the vein, and FIG. 11C is sectional view 11C-11C of FIG. 11B.

More specifically, FIGS. 11A-11C illustrate the use of patch 700 to enlarge and reinforce a vein V. First, the side of vein V distal from the skin is provided with a longitudinal opening, indicated as incision I in FIG. 11A. Next, with the incision held open to increase the diameter of the vein, the edge of the patch is sewn about the incision. Thus, FIGS. 11B and 11C, show stitches 1101 that join the material 102 of patch 700 to the edges of the incision on the interior surface of the vein, with reinforcement 701 spanning the open portion of the incision, and thus increasing the size of the vein's lumen. In certain embodiments, reinforcement 701 has a semicircular shape that generally matches the tubular shape of the vein. As illustrate in FIGS. 11B and 11C, patch 700 thus enlarges the diameter of the vein at the patch and reinforces the patched vein with reinforcement 701. Alternatively, patch 700 may be sewn to the outer surface of the vein.

In certain embodiments, a patch, such as patch 100, 300, 500, 700, 900 or 1100 forms part of a cylinder, and thus wraps part way around the circumference of the fistula.

In certain embodiments, the patch is formed from a single material. Thus, for example, a reinforcement, such as reinforcement 910 may be applied to the patient directly, for example, by stitching through holes 913 and into a side of fistula F.

In one embodiment, a patient may be provided with a first patch through which a needle may be inserted for hemodialysis, such as patch 100, 300, 500, 700, 900 or 1100, which is provided on a proximal side of fistula F, and with a second patch located on the opposite, distal side of the fistula, such a patch 700 or 900. A needle connected to the catheter of a hemodialysis machine is then inserted through the first patch and into the fistula of the patient and is prevented from puncturing the fistula by the second patch.

In another embodiment, hemodialysis may be provided to a patent by forming a fistula from an artery and a vein of the patient, as is known in the art, and then covering at least a portion of the outer surface of the fistula with a patch, which may be similar to patch 100, 300, 500, 700, 900 or 1100. A needle connected to the catheter of a hemodialysis machine is then inserted through the patch and into the fistula of the patient.

In yet another embodiment, a device is provided for preparing a fistula of a patient for hemodialysis. The device includes a patch, which may be similar to patch 100, 300, 500, 700, 900 or 1100 comprises a layer of a biocompatible material, where the patch is sized to cover a portion of the outer surface of the fistula.

In certain embodiments, patch 100, 300, 500, 700, 900 or 1100 may be felt though the skin of the patient. This allows the person inserting the needle into the patient to determine the location of patch by palpation, and thus makes it easier to inert the needle at the proper location.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

I claim:

1. A patch for a blood vessel comprising:
   a rigid portion having an inner surface and an outer surface,
   where said inner surface is a portion of a cylindrical shape and has an inner surface area bounded by one inner surface edge, where said inner surface has a length extending along a longitudinal direction of the cylindrical shape and a width extending circumferentially around a circumference of the cylindrical shape, and where said outer surface opposes the inner surface,
   such that when the inner surface of the patch contacts an exterior wall of the blood vessel, the inner surface contacts an area of the exterior wall equal to the inner surface area.

2. The patch of claim 1, where said rigid portion is biocompatible.

3. The patch of claim 1, where said rigid portion includes a metal.

4. The patch of claim 3, where said metal is stainless steel or titanium.

5. The patch of claim 1, where the rigid portion has a thickness of between 0.25 mm and 1.00 mm.

6. The patch of claim 1, where said inner surface includes three-dimensional features.

7. The patch of claim 6, where said three-dimensional features include a roughened surface, protuberances on the surface, or a plurality of holes through the patch.

8. The patch of claim 6, where the three-dimensional features have a dimension of from 0.25 mm to 2 mm.

9. The patch of claim 1, where the width extends circumferentially about the circumference of the cylindrical shape by from 70 degrees to 180 degrees.

10. The patch of claim 1, where the width extends circumferentially about the circumference of the cylindrical shape by from 70 degrees to 90 degrees.

11. The patch of claim 1, where the width extends circumferentially about the circumference of the cylindrical shape by from 90 degrees to 120 degrees.

12. The patch of claim 1, where the width extends circumferentially about the circumference of the cylindrical shape by from 120 degrees to 150 degrees.

13. The patch of claim 1, where the width extends circumferentially about the circumference of the cylindrical shape by from 150 degrees to 180 degrees.

14. A patch for a blood vessel comprising:
    a rigid portion having an inner surface and an outer surface,
    where said inner surface is a portion of a cylindrical shape and has an inner surface area bounded by one inner surface edge, where said inner surface has a length extending along a longitudinal direction of the cylindrical shape and a width extending circumferentially around a circumference of the cylindrical shape, and where said outer surface opposes the inner surface,
    where the rigid portion includes stainless steel or titanium, and
    where said inner surface includes three-dimensional features having a dimension of from 0.25 mm to 2 mm,
    such that when the inner surface of the patch contacts an exterior wall of the blood vessel, the inner surface contacts an area of the exterior wall equal to the inner surface area, and
    such that the patch inhibits needles from moving along the inner surface.

15. The patch of claim 14, where said three-dimensional features include a roughened surface, protuberances on the surface, or a plurality of holes through the patch.

16. The patch of claim 14, where the rigid portion has a thickness of between 0.25 mm and 1.00 mm.

17. The patch of claim 14, where the width extends circumferentially about the circumference of the cylindrical shape by from 70 degrees to 180 degrees.

18. The patch of claim 14, where the width extends circumferentially about the circumference of the cylindrical shape by from 70 degrees to 90 degrees.

19. The patch of claim 14, where the width extends circumferentially about the circumference of the cylindrical shape by from 90 degrees to 120 degrees.

20. The patch of claim 14, where the width extends circumferentially about the circumference of the cylindrical shape by from 120 degrees to 150 degrees.

21. The patch of claim 14, where the width extends circumferentially about the circumference of the cylindrical shape by from 150 degrees to 180 degrees.

* * * * *